(12) United States Patent
Reznicek et al.

(10) Patent No.: US 6,890,100 B2
(45) Date of Patent: May 10, 2005

(54) CT GANTRY BALANCE SYSTEM

(75) Inventors: Mark Edmund Reznicek, Waukesha, WI (US); Eric Matthew Plate, Waukesha, WI (US); Shawn Patrick Faessler, Hartland, WI (US)

(73) Assignee: GE Medical Systems Global Technology, Inc., Waukesha, WI (US)

( * ) Notice: Subject to any disclaimer, the term of this patent is extended or adjusted under 35 U.S.C. 154(b) by 104 days.

(21) Appl. No.: 10/604,422

(22) Filed: Jul. 18, 2003

(65) Prior Publication Data

US 2005/0013403 A1 Jan. 20, 2005

(51) Int. Cl.$^7$ ............... G01D 18/00; G01M 1/08; G01M 1/16
(52) U.S. Cl. ............... 378/207; 378/15; 378/162; 73/458; 73/459; 73/462; 73/468
(58) Field of Search ............... 378/4, 15, 162, 378/205, 207; 73/457–462, 468–470

(56) References Cited

U.S. PATENT DOCUMENTS

| | | | | |
|---|---|---|---|---|
| 5,432,339 | A | * 7/1995 | Gordon et al. | 250/231.13 |
| 5,448,608 | A | * 9/1995 | Swain et al. | 378/4 |
| 5,627,762 | A | * 5/1997 | Cameron et al. | 700/279 |
| 6,412,345 | B1 | * 7/2002 | Murray et al. | 73/468 |
| 6,590,960 | B2 | 7/2003 | Kroener et al. | 378/162 |
| 6,748,806 | B2 | * 6/2004 | Halsmer | 73/462 |

* cited by examiner

*Primary Examiner*—Allen C. Ho (57) ABSTRACT

A method and system for balancing CT gantry mechanisms. Two balance locations are preselected on the rotating base member and stacks of spacers, shims, and weights are provided at each site. Strain gate sensors are provided on the stationary base member and included as part of a sensor circuit. Trial and test runs determine the mass and Z-location of the mass which needs to be added to the system to statically and dynamically balance it.

16 Claims, 6 Drawing Sheets

CT GANTRY BALANCE SYSTEM

BACKGROUND OF INVENTION

The present invention relates to CT systems and more particularly to methods and systems for balancing CT gantry members.

Computed Tomography ("CT") systems are in wide use today. The CT systems take X-ray images of objects or persons in order to provide scientific and/or medical information. In general, CT systems include a large gantry mechanism positioned in a housing with an annular opening in which the object or person is positioned. The gantry mechanism includes a rotating base member on which an X-ray tube and detector plate are mounted. As the base member rotates and the object or person is moved along the axis of rotation, X-ray images are taken for later analysis.

The rotating base member typically has other system components mounted on it, such as a heat exchanger and generator. The X-ray tube, detector plate, and other components rotate with the base member. It is important to balance the rotating base member so that it revolves uniformly and provides satisfactory, high quality images.

Imbalance of the rotating portion of a CT gantry results in an oscillatory motion of the entire gantry mechanism at a frequency of once per revolution. This motion is detrimental to the quality of the images and can generate artifacts when the motion is increased above a certain threshold. Typically, CT gantry mechanisms are balanced in the factory where the CT systems are built and calibrated, before they are shipped to their ultimate destinations. The CT systems are also balanced in the field, typically when components are replaced for service, such as a new X-ray tubes. The field balance is particularly important in order to assure accurate performance of the CT system. At the present time, however, methods and systems used to balance gantry mechanisms in the field have shortcomings. Thus, there is a need for improved systems and methods for balancing CT gantry mechanisms, particularly for balancing the mechanisms in the field.

SUMMARY OF INVENTION

The present invention comprises an improved method and system for balancing of CT gantry mechanisms, both in the factory and in the field. With the present invention, CT gantry mechanisms can be both statically and dynamically balanced, even in field situations. With the present method, both static and dynamic imbalance can be measured and, if necessary, eliminated. The present invention results in reduction in time and complexity for the user compared with existing CT static balancing methods.

With the present invention, balance weights are added at two pre-selected sites on the rotating base member of the CT gantry mechanism. The two sites are approximately 90° apart. Elongated rod members are provided at the two sites on which to position various balance weights, spacers, and shims as necessary to balance the CT system. The weights, spacers, and shims allow changing of the Z-axis coordinate of the imbalance in order to provide the correct weight at the correct Z coordinate.

Preferably, the two sites are provided in the lower left quadrant of the rotating base member when viewed from the front of the CT gantry mechanism. These sites are preferred due to the need to balance the weight of the x-ray tube and for static and dynamic balance adjustments.

Strain gages are provided on the stationary base member of the gantry mechanism at locations where the imbalance induces relatively high strains. The strain gages are connected to a balance sensor circuit, which is connected to the gantry processor. Firmware is used to sample the output from the sensors at a prespecified sampling rate.

Strain measurements are first taken during a baseline run with the weights as installed in the factory in order to have a base of reference. Additional measurements are then taken with trial runs with trial weights at known locations. These baseline and trial measurements are then used in order to calculate the amount of weight which needs to be added at the two preselected sites, and their location along the Z-axis. The final total forces and moments of the system are calculated and new configurations for each of the two stacks of weight are determined which will produce those total forces and moments. The appropriate configuration of weights, spacers, and shims are then positioned on the rod members at the two preselected locations on the rotating base member. Steel plates of two different thicknesses are utilized to provide the bulk of the weight. Light aluminum spacers and shims are used to center the mass of the stack at the target Z-location. Small weights are used to provide fine adjustments in the mass as necessary. With the present invention, the specific amount of weights, spacers, and shims, both in quantity and arrangement, is provided from the calculations.

With the present invention, static and dynamic balancing of the rotating base members of CT gantry systems can be provided, both in the factory and in the field. Also, specific instructions to the user are provided with the present system in order to eliminate guess work and provide accurate balancing. Having just two locations for balance weights rather than numerous sites is also a benefit and provides for easier adjustment in the field. Finally, with the present invention, a finite number and types of balance weights are needed.

The above objects and other objects, features, and advantages of the present invention are readily apparent from the following detailed description of the preferred embodiments for carrying out the invention when taken in accordance with the accompanying drawings.

DETAILED DESCRIPTION

Figure 1:
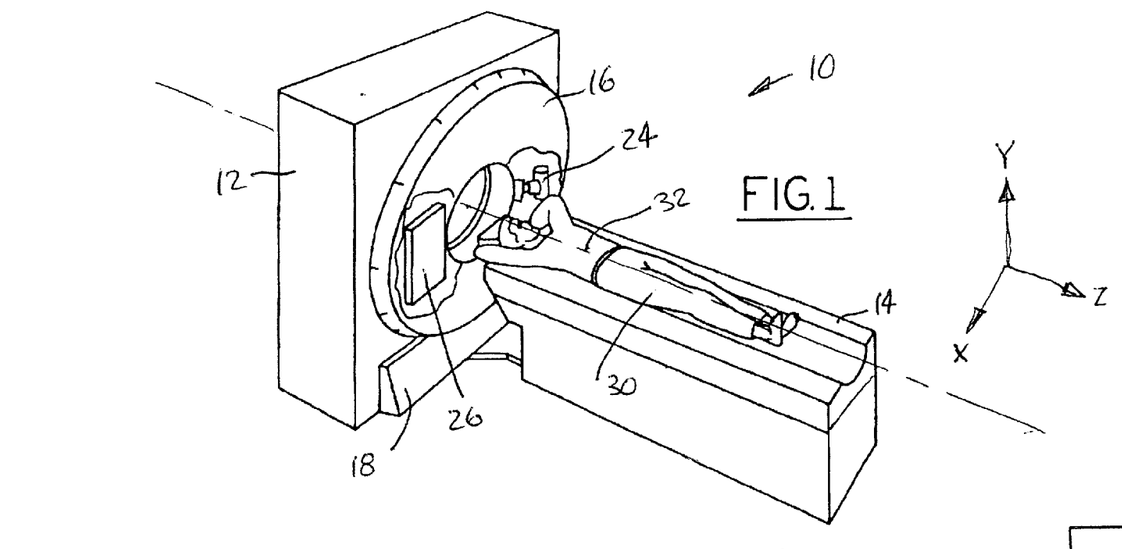
FIG. 1 schematically illustrates a conventional CT system.

A conventional CT system is shown in FIG. 1 and referred to generally by the reference numeral 10. The CT system includes a gantry member 12 and a patient table member 14. The gantry member 12 includes an annular portion 16 and a base portion 18. A rotating base member 20, as shown in FIGS. 2–5, is positioned inside the annular portion 16, while a stationary base member 22 is positioned inside the base member 18.

In accordance with standard CT systems, an x-ray tube and collimator 24 is positioned on the rotating base member 20 together with a detector plate member 26. A patient 30 or other object is positioned on the table member 14 and moved along the Z-axis 32 which is the axis of rotation of the rotating base member 20 and gantry member 12. The x-ray tube member 24 and detector plate member 26 are positioned opposite one another on the gantry member and x-ray images of the patient 30 or object on the table member 14 are made as the table member moves through the central opening of the gantry member 12.

Figure 2:
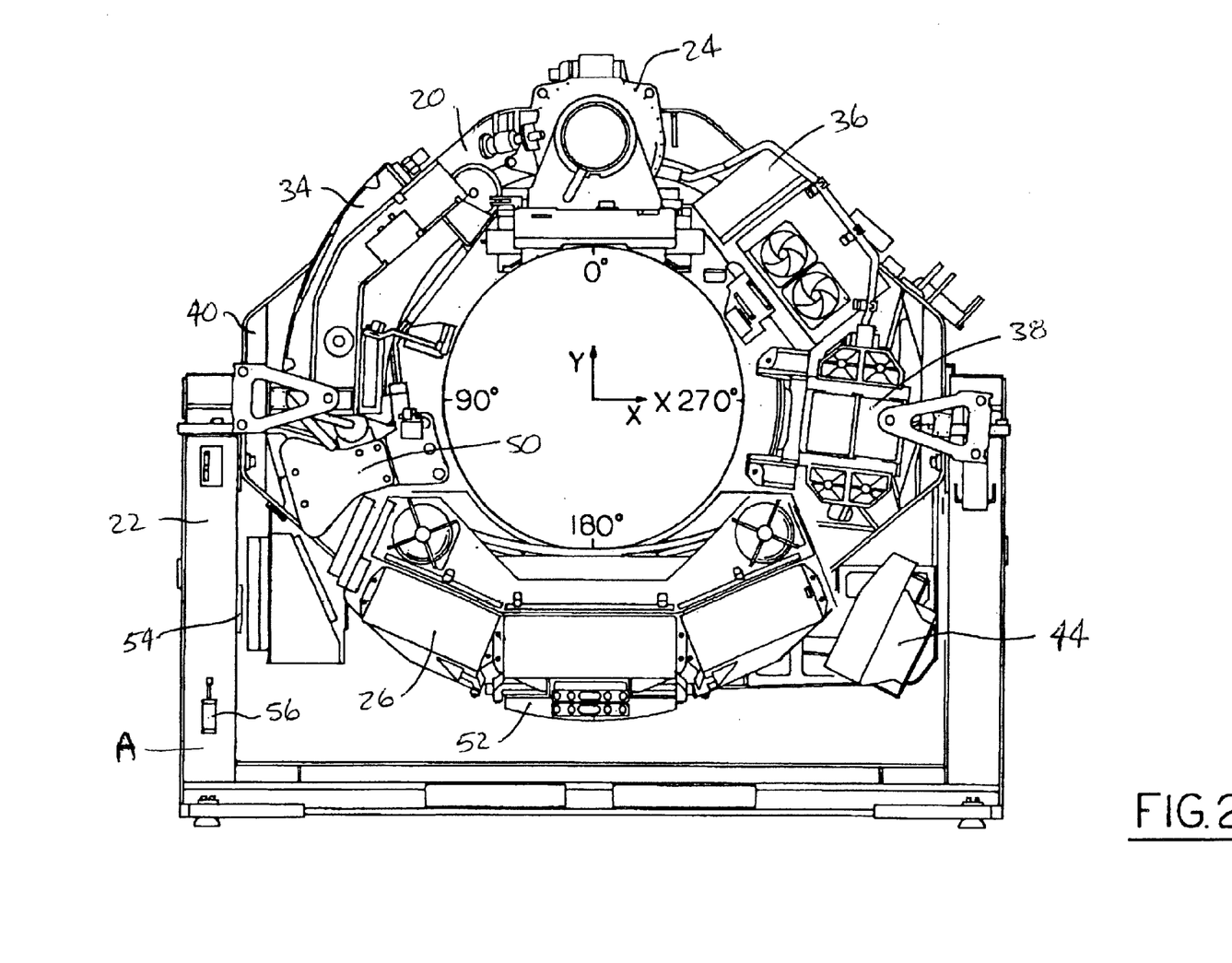
FIG. 2 is a front view of a gantry mechanism (without a cover), including the rotating and stationary base members.
Figure 3:
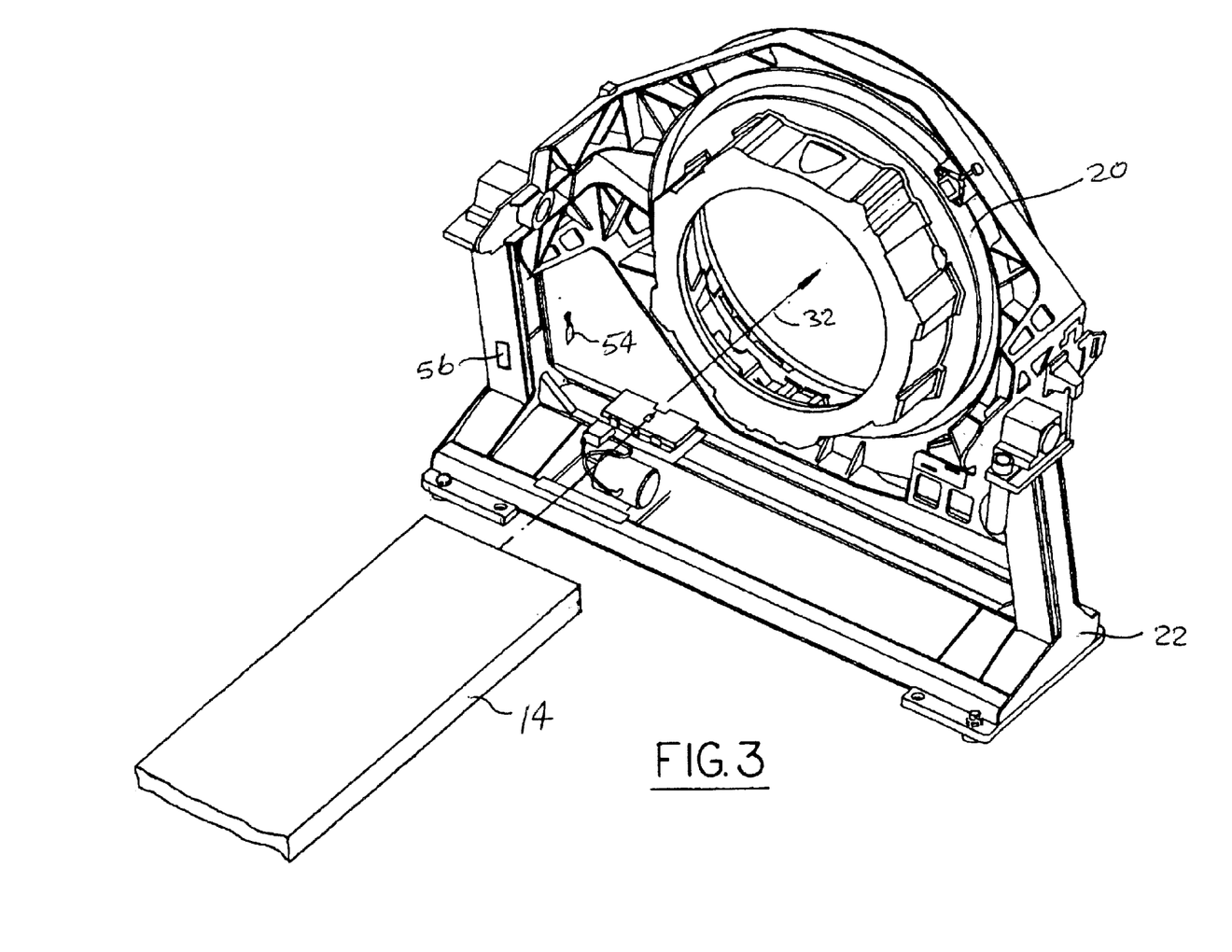
FIG. 3 is a perspective view of the gantry mechanism shown in FIG. 2, with several of the components removed for clarity.

As shown in FIG. 2, several components and accessory members are positioned on the rotating base member 20. These typically include a heat exchanger 34, a high voltage generator 36, and a high voltage tank 38. Also, as is common with CT systems, an axial bearing and slip ring (not shown) are attached to the rotating base member 20. A bearing bracket 40 is used to attach the axial bearing to the stationary base member 22. The slip ring is attached to bracket members 42 which are shown in more detail in FIGS. 4 and 5. Electrical power is supplied to the electrical components on the rotating base member through the slip ring and slip ring brushes as typical in CT systems.

An axial motor assembly 44 is utilized to rotate the base member 20 relative to the stationary base member 22.

The relative positions of the components on a rotating base member are often indicated by degrees from the twelve o'clock position. This is shown in FIG. 2, where the zero degree point is indicated at the twelve o'clock position. In accordance with the system used with the present invention, the degrees are measured counter-clockwise when the gantry member is viewed from the front. Thus, the 90° position is loaded at the nine o'clock position, and the 180° position is located at the six o'clock position, etc.

Figure 4:
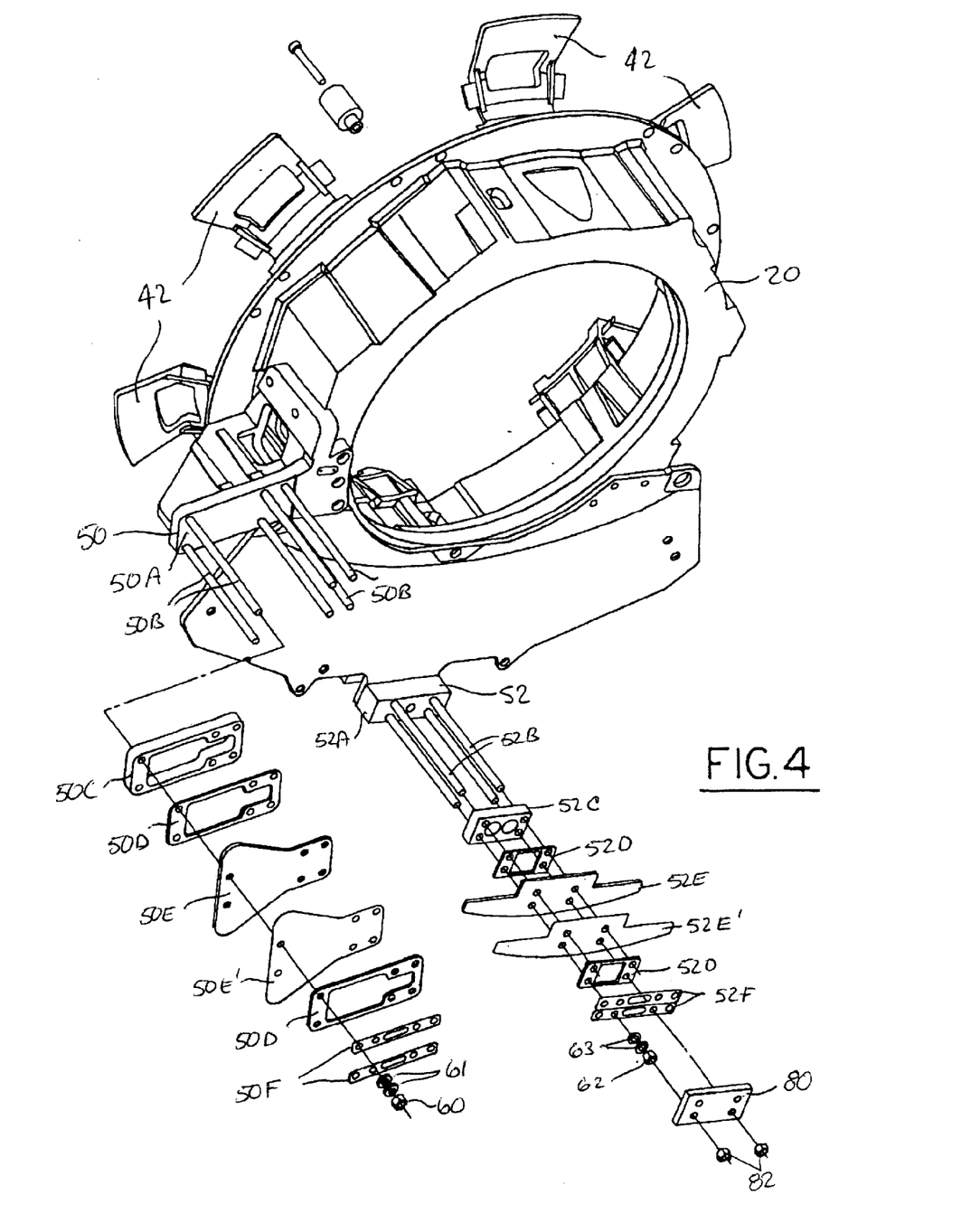
FIG. 4 is a perspective exploded view of a rotating base member illustrating balancing components utilized in accordance with the present invention.

With the present invention, balance weight systems are utilized at two pre-selected sites 50 and 52, as particularly shown in FIGS. 2 and 4. Also, a pair of strains gage sensors 54 and 56 are mounted on the stationary base member 22, preferably adjacent the bottom or lower portion.

Due to the weight of the various components, which are positioned on the rotating base member 20, and their relative positions, the gantry member is typically unbalanced when it rotates. This imbalance is both in the X-axis and Y-axes directions, as well as the Z-axis direction.

Imbalance of the rotating portion of a CT gantry mechanism results in an oscillatory motion of the entire gantry at a frequency of once per revolution. This motion is detrimental to image quality, as it can generate artifacts when the motion is increased above some threshold. This imbalance is first minimized in the factory where the CT system is built and calibrated. The balance needs to be restored in the field when components are replaced for service. Balancing of the gantry in the factory is easier and more accurate with known systems since all of the balancing equipment and systems are readily available. In the field, however, balancing is difficult due to the lack of tools and systems that are needed for accurate balancing.

Two-plane balancing of a CT gantry (i.e. static and dynamic balancing) is difficult since there is no continuous plane onto which to attach or from which to remove weights. The output from a two-plane balance procedure comprises four values. These are the mass and angular location of weights which need to be attached to or removed from the system on each of the two-planes to balance the system. Each plane is defined to be the Z-coordinate of each trial weight. By convention, the Z-axis is the rotational axis of the gantry.

By using equations for force and moment caused by the imbalance, the four values can be treated as variables and exchanged for the four different valuables so long as the forces and moments remain unchanged. In this regard, the mass and Z-coordinates of the two balance weights are changed by pre-selecting the angles at which to add the two masses. This obviates the problem of needing the continuous plane with an infinite number of places for attaching balance weights. The Z-coordinate of the mass is made variable by using spacers and shims, particularly made of a lightweight material, such a aluminum, together with stacks of heavier balance weights, particularly made of a steel material. The spacers and shims are utilized to position the balance weights at their correct Z-coordinates.

For one preferred gantry member, such as the General Electric Hpower gantry, the balance weight positions are 107° and 180° (see FIG. 2). These sites particularly balance the weight of the x-ray tube, which is a large mass and which can be relocated for alignment. Also, the sites are approximately 90° apart in order to provide proper static and dynamic balance adjustment. In this regard, with the present invention, it is preferred that the two sites be approximately 90° apart, although the precise position of the balance weights depend upon the particular system utilized.

The imbalance of the rotating base member is measured by the two strain gage sensors 54 and 56. The strain gages preferably are made of piezoceramic material and are self-energized, although any equivalent type of strain gages can be utilized.

As shown in FIGS. 2 and 4, each of the weight systems 50 and 52 include a base member 50A and 52A, respectively, and a plurality of rod members 50B and 52B, respectively, for holding the balancing members. The weight systems 50 and 52 also possibly can include one or more spacer members 50C and 52C, respectively, one or more shim members 50D and 52D, respectively, one or more heavy weight members 50E and 52E, respectively, one or more lighter weight members 50E' and 52E', respectively, and one or more trim members 50F and 52F, respectively. The rod members 50B and 52B are preferably threaded rod members, such that the balance and weight members are held on the rod members by threaded fasteners, such as nuts 60 and 62. Although only one nut member, together with associated washer members 61 and 63, is shown in FIG. 4, it is understood that similar sets of nuts and washer members are utilized on all of the rod members 50B and 52B.

The weights are used to balance the rotating base member along all three of the X, Y, and Z axes directions. The spacers and shims are used to shift the weights along the Z-axis direction.

Also, as shown in FIG. 4, six rod members 50B and four rod members 52B are preferably utilized in order to accurately and securely hold the weights, spacers, and shim members in place. It is to be understood, of course, that any number of rod members can be utilized or provided. Also, the sizes and weights of the various spacers, shims and weights can be utilized as are necessary and required for each of the CT systems. In this regard, with the present invention, the spacer and shim members are made from a lightweight material, such as aluminum, while the weight members are made from a heavier material, such as steel.

When the accessories and electronic components are added to the rotating base member 20, and that base member is rotated, the stationary base member 22 flexes slightly in the X and Y directions, as well as along the Z direction. From experience, it is found that the stationary base member 22 stretches or moves the most adjacent the bottom or lower portion "A" when the rotating base member 20 is rotated. Thus, with the preferred embodiment of the present invention, the strain gage sensors 54 and 56, are positioned in that area A.

Figure 5:
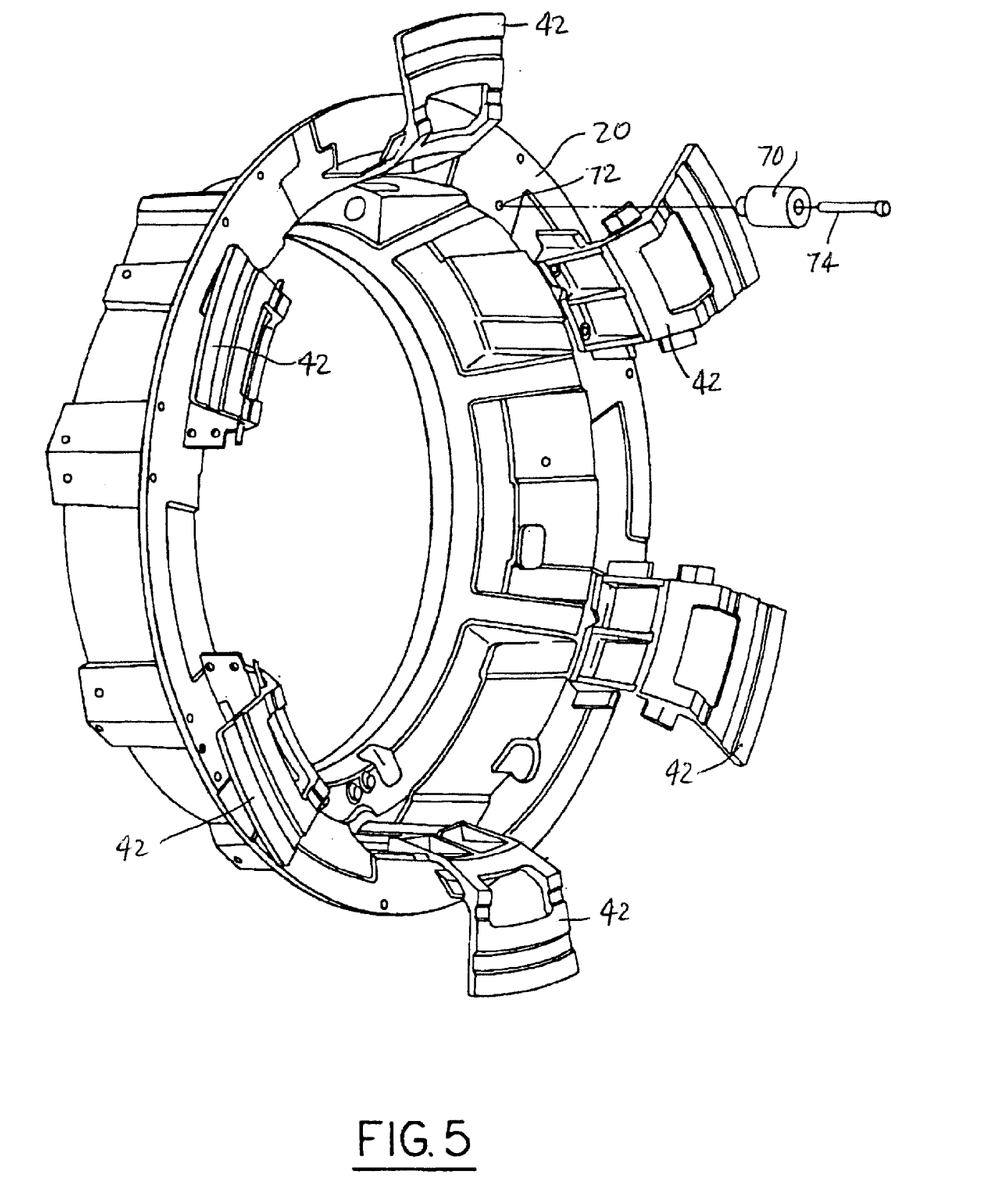
FIG. 5 is a rear view of the rotating base member.

As an initial step in balancing a CT gantry mechanism, trial weights are positioned on the rotating base member, and one or more baseline runs are used to measure the sensitivity of the system to known imbalances. This involves the usual two-plane method and calculates the imbalance, magnitude and phase angle for each plane. For this purpose, a trial weight 70 is attached to the rotating base member 20 at location 72, as shown in FIG. 5. The trial weight 70 is attached by a fastener, such as a set screw 74, and positioned at a known location. With the preferred embodiment of the present invention, the location 72 is at the 36° position, as viewed from the front in FIG. 2. In addition, second trial run is conducted with a trial weight at another preselected location. In this regard, with one embodiment of the present invention, a trial weight 80 is attached to the rod members 52B at the 180° position and secured with nut members 82.

Figure 6:
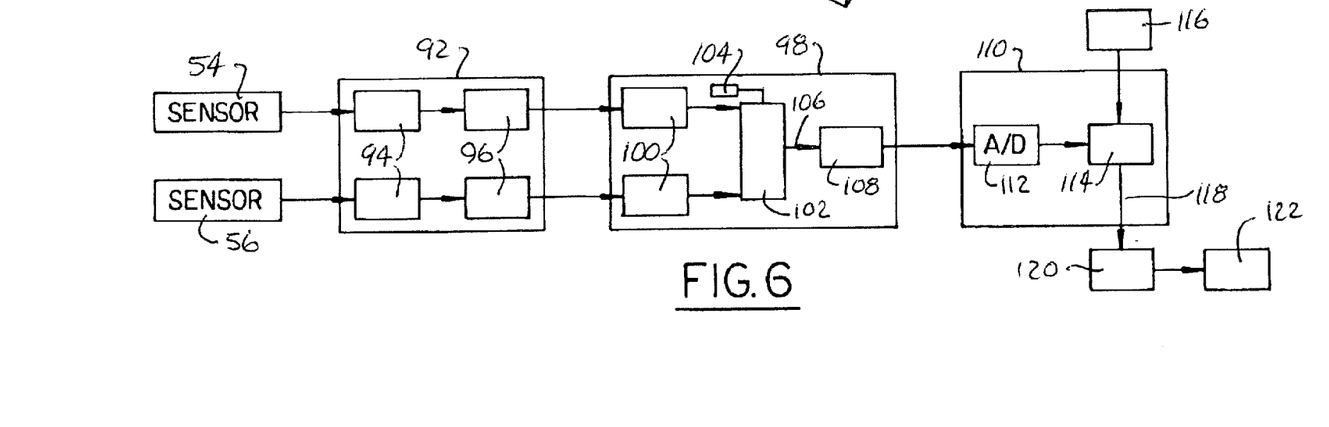
FIG. 6 is a schematic diagram of a balancing circuit which can be utilized with the present invention.

As indicated, the strain gages 54 and 56 are attached to the lower portion of the stationary base member 22, where the imbalance of the rotating base member 20 induces relatively high strains. FIG. 6 depicts a circuit diagram in which the two strain gage sensors 54 and 56 are positioned. Strain gage sensor 54 measures strain in the X-axis direction, while strain gage sensor 56 measures strain in the Z-axis direction. The input from the strain gage sensor 54 and 56 is first passed through a balance sensor buffer board 92 which includes a pair of high pass filters 94 and gain members 96. These signals are then sent to a subordinate board 98, which includes filter members 100 and a multiplexer 102. The multiplexer also has a select function 104. The signal 106 from the multiplexer is then affected by a reference voltage offset 108 and sent to a table gantry processor 110. The processor 110 includes an analog-to-digital converter 112 and a microprocessor 114. The microprocessor 114 is loaded with firmware 116 in order to make the necessary calculations. The output of 118 of the microprocessor is sent to a monitor 120 and optionally to a printer 122 in order to display and optimally print out the appropriate balancing calculations and instructions.

The firmware 116 is used to sample the output from the sensors at a fixed sampling rate, such as 40 samples per second. The sample data is written to a file. The once-per-revolution portion of the signal is extracted as a vector (magnitude and phase angle) for each of the two sensors using a least squares method. The least squares method makes it possible for the firmware program to provide the gantry angle at the instant that each strain gage is sampled. The least squares method is also more robust and does not rely on the data being exactly equally spaced in time compared to a Fourier-based approach. However, the method results in the usual Fourier-based equations when the data is equally spaced in time.

As indicated above, the strain gage measurements are made during a baseline run (i.e. original imbalance) on the gantry, and the once-per-revolution vectors in the X-axis and Z-axis directions are computed. Then, the usual two trial runs are made, each with a trial weight at a known location and the once-per-revolution vectors are extracted ($X_1$, $Z_1$, $X_2$, $Z_2$). From these vectors, a sensitivity matrix is determined. Complex numbers are used since this provided a natural method to work with magnitude and phase angles of the vectors. The sensitivity matrix and the identity of the X and Z components are set forth below:

$$\begin{bmatrix}X \\ Z\end{bmatrix} = \begin{bmatrix}a_{11} & a_{12} \\ a_{21} & a_{22}\end{bmatrix}\begin{bmatrix}U_a \\ U_b\end{bmatrix} \Rightarrow \begin{bmatrix}U_a \\ U_b\end{bmatrix} = \begin{bmatrix}a_{11} & a_{12} \\ a_{21} & a_{22}\end{bmatrix}^{-1}\begin{bmatrix}X \\ Y\end{bmatrix}$$

$$a_{11} = \frac{X_1 - X}{U_{aT}} \quad a_{12} = \frac{X_2 - X}{U_{bT}} \quad a_{21} = \frac{Z_1 - Z}{U_{aT}} \quad a_{22} = \frac{Z_1 - Z}{U_{bT}}$$

X=strain from sensor 54 during baseline run (magnitude and phase or real and imaginary $X_1$=strain from sensor 54 during the first trial run $X_2$=strain from sensor 54 during the second trial run Z=strain from sensor 56 during the baseline run $Z_1$=strain from sensor 56 during the first trial run $Z_2$=strain from sensor 56 during the second trial run $U_{aT}=M_{aT}R_{aT}\angle\theta_{aT}$  $U_{bT}=m_{bT}R_{bT}\angle\theta_{bT}$  $U_a=m_a R_a\angle\theta_a$  $U_b=m_b R_b\angle\theta_b$ The sensitivity matrix [$\alpha$] can be stored and re-used at a later. It is a function of the gantry structure and not the imbalance and thus will not change over time. It can be re-used to simply check the balance condition, for instance, when a component has been replaced. It can also be re-used to solve for a new stack configuration of weights when a component change results in an imbalance which is outside the specifications. The re-use saves time needed to balance the system since trial weights do not need to be attached.

Once $U_a$ and $U_b$ are known, the mass and Z-axis location of the mass which needs to be added to the system to statically and dynamically balance the system can be calculated. The stack forces and moments caused by the mass of the original stack on the gantry during the baseline and trial runs is calculated and combined with the forces and moments caused by the mass and center of mass which is needed to balance the gantry. These are the final total forces and moments.

A new configuration of each stack is then determined which produces the same total forces and moments. The new configuration is composed of spacers, shims, thick metal weights, thin metal weights and trim weights. The new configuration is determined by a software program which converges to the solution for each of the two stacks of weights 50 and 52 independently.

The solver starts with the target mass and center of mass location. First the spacers 50C and 52C are positioned on the rod members. The spacers are used to provide coarse adjustment of the Z-axis location of the weights. The weights 50E, 50E' and 52E and 52E' are then utilized as needed together with the shim members 50D and 52D provided with the system. Preferably, nine aluminum shims are provided for each of the balance weight systems 50 and 52. The shims can either straddle the weight members, be clustered on the spacer side of the weights, or clustered on the side of the weights away from the spacers. The shims are used to provide fine adjustment in the Z-axis location of the weight members.

The algorithm is then solved for a combination of thick weights, thin weights, and trim weights, which meets the mass target value, including the small mass of the spacers and shims. The shims are then moved incrementally toward the spacers to shift the center of mass towards the target Z-axis coordinate until all the shims are against the spacer or the target Z-axis coordinate is achieved. Each time a shim is moved, the algorithm is solved for a combination of the various weight balancing components. Thereafter, if the Z-axis target is not met, the spacers and shims are moved, and the process is repeated until both the target mass and target Z-axis coordinate are achieved.

The design of the balance stacks allows a range of mass and Z-axis coordinates of the center of mass with sufficient adjustability to cover the range of possible imbalances. Some of the equations used by the solver program and algorithm are as follows:

Forces:

$$F_x = -Im(U_a) - Im(U_b)$$

$$F_y = Re(U_a) + Re(U_b)$$

Moments:

$$M_x = (Z_{piv} - Z_a)Re(U_a) + (Z_{piv} - Z_b)Re(U_b)$$

$$M_y = (Z_{piv} - Z_a)Im(U_a) + (Z_{piv} - Z_b)Im(U_b)$$

Static and Dynamic imbalance:

$$St = \sqrt{F_x^2 + F_y^2} \quad Dy = \sqrt{M_x^2 + M_y^2}$$

Balance stack mass;

$$m_{107} = \frac{F_x}{\overline{Y}_{107}} \quad m_{180} = \frac{F_y - m_{107}\overline{Y}_{107}}{\overline{Y}_{180}}$$

Z-axis coordinate to center of mass of each balance stack:

$$\overline{Z}_{107} = z_{piv} + \frac{M_y}{m_{107}\overline{X}_{107}}$$

$$\overline{Z}_{180} = z_{piv} + \frac{M_x - m_{107}\overline{Y}_{107}(\overline{Z}_{107} - z_{piv})}{m_{180}\overline{Y}_{180}}$$

Pre-defined masses and spacers are used to prevent the need for weighing and measuring the individual parts. The solver algorithm is constructed so that it will converge to a balance state given the tolerances in the spacers, shims, and weights (both in thickness and in mass).

Each balance stack 50 and 52 is composed of weight plates of two different thicknesses in order to provide the bulk of the weight. The light aluminum spacers and shims are utilized to move the center of mass of the stack to the target Z-axis location. The trim weights are used to provide the final adjustment in the mass.

The solver algorithm is implemented as a service tool with software on the table gantry processor 110. This solves for the exact combination of elements to make each stack of the required mass and target Z-axis coordinate. The output of the present invention is given to the user through the screen 120 and printer 122 in terms of the exact recipe, both in quantity and arrangement, of spacers, shims, thick weights, thin weights, and trim weights. This results in a reduction in time and complexity for the user. The user does not have to measure the mass and center of mass in the field.

A twice-per-revolution signal is then used to check for a broken strain gage sensor. The twice-per-revolution signal is normal for a gantry and is not affected significantly by any imbalance. If the twice-per-revolution signal falls below a set level, however, the user is alerted to check for a problem in the sensors or the circuitry.

The variable $Z_{piv}$ is the location of the center of mass of the rotating system. If the mass is added on this plane, dynamic imbalance will not be changed. Typically, only an estimate of the value is needed with the present invention.

The present invention can be used either in the field or the factory, or both. It provides portability, which particularly allows balancing of the rotating base member and gantry in the field.

The present invention eliminates guess work which is needed in two-plane balancing of a CT gantry. The two balance planes do not generally have the same Z-axis coordinate as the few locations where balance weights can actually be attached to the gantry. This reduces the training needed by a user.

The present invention also simplifies gantry designs since only two locations for balance weights are set aside rather than numerous sites for holding balance weights. Also, a finite number and type of balance weights are utilized.

The preselection of the two balance locations on the gantry and the use of "shifting method," simplifies balancing CT gantries. Known approaches use a variety of locations to add balance weights to statically balance a gantry by splitting the one-plane solution (mass and phase angle) to the nearest sites. With the present invention, the static and dynamic balance can be sent simultaneously.

The present invention utilizes an algorithm to calculate the exact combination of spacers, shims, thick plates, thin plates, and trim weights to balance the system. The average weight and average thickness of each of the types of spacers, shims, plates and trim weights are provided in the algorithm so the user is not burdened with providing such information. Strain gage sensors are also utilized which provide a relatively large signal and are self-energized for simplicity.

Figure 7:
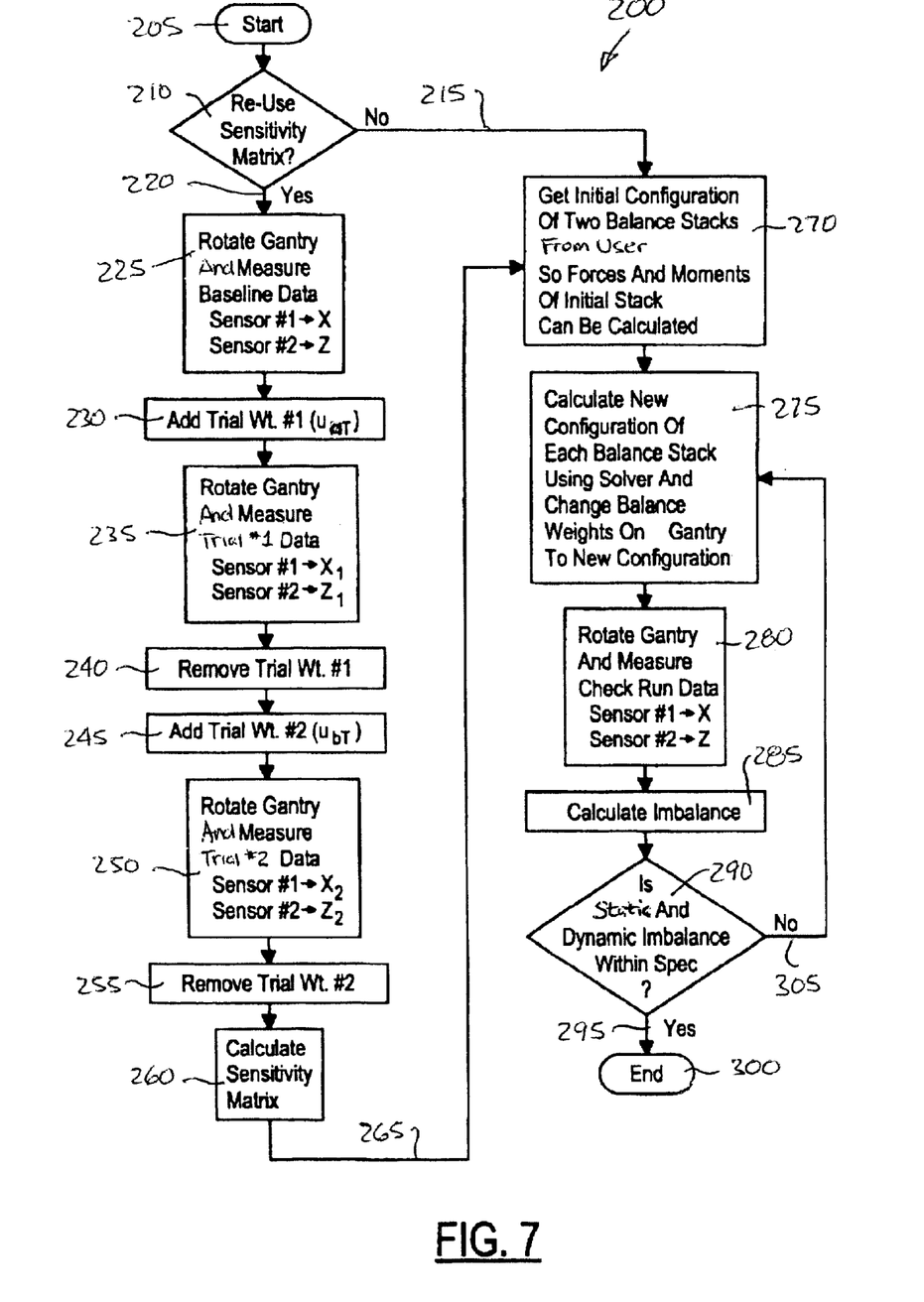
FIG. 7 is a flow diagram illustrating a preferred method of use with the present invention.

A flow diagram schematically illustrating a preferred embodiment of the method of the present invention is depicted in FIG. 7 and designated generally by the reference numeral 200.

While the invention has been described in connection with one or more embodiments, it is to be understood that the specific mechanisms, processes and procedures which have been described are merely illustrative of the principles of the invention, numerous modifications may be made to the methods and apparatus described without departing from the spirit and scope of the invention as defined by the appended claims.

What is claimed is:

1. A system for balancing a CT gantry mechanism having a stationary base member and a rotating base member, the rotating base member rotating about a Z-axis and having an x-ray tube and detector plate positioned thereon, a first weight stack mechanism having a first known plurality of weight members and spacers, a second weight stack mechanism having a second known plurality of weight members and spacers, said first and second stack members being positioned on said rotating base member at a pre-selected positions, and a pair of strain gage sensors positioned on said stationary base member adjacent said rotating base member.

2. The system as described in claim 1 wherein said spacers comprise individual spacer members and individual shim members.

3. The system as described in claim 1 wherein said weight members comprise a first set of individual weight members having a first mass and a second set of individual weight members having a second mass different from said first mass.

4. The system as described in claim 1 wherein said pre-selected positions are approximately 90° apart.

5. The system as described in claim 1 wherein said pre-selected positions are situated at the approximately 107° and 180° positions on said rotating base member, said positions be measured counterclockwise from a 0° position on said rotating base member.

6. The system as described in claim 1 wherein said strain gage sensors are made from a piezoceramic material.

7. A system as described in claim 1 wherein said pair of strain gage sensors comprise a first strain gage sensor to sense strain in the X-direction and a second strain gage sensor to sense strain in the Z-direction.

8. A method for balancing a CT gantry mechanism having a stationary base member, a rotating base member rotating about a Z-axis, and with an x-ray tube and detector plate positioned on said rotating base member, the method comprising the steps of: providing a first plurality of individual weight members and spacers at a first pre-selected location on said rotating base member; providing a second plurality of individual weight members and spacers at a second pre-selected location on said rotating base members; positioning trial weights on said rotating base member; conducting a first baseline run, measuring the imbalance of the CT gantry mechanism and calculating the imbalance magnitudes and phase angles; conducting two additional trial runs with trial weights positioned at prespecified locations on said rotating base member; calculating the mass and Z-axis location of the mass necessary to statically and dynamically balance said mechanism; and positioning the first and second plurality of weight members and spacers in order to meet said calculations.

9. The method as described in claim 8 wherein said spacers comprise individual spacer members and shim members.

10. The method as described in claim 8 wherein said individual weight members comprise a first set of weight members having a first mass and a second set of weight members having a second mass different from said first mass.

11. The method as described in claim 8 wherein said pre-selected locations of said first and second plurality of weight members and spacer members are approximately 90° apart.

12. A method as described in claim 8 wherein said pre-selected location of said first and second plurality of weight members and spacer members are at the 107° and 108° locations on said rotating base member, said positions be measured counterclockwise from a 0° position on said rotating base member.

13. A method as described in claim 8 wherein said calculating the mass and Z-axis are carried out with a processor.

14. A method as described in claim 8 further comprising the step of adjusting said positioning said first and second plurality of weight members and spacers in order to finalize the balancing.

15. The method as described in claim 8 further comprising the step of conducting a test to check the performance of the balancing.

16. The method as described in claim 8 wherein said measuring the imbalance of the CT gantry mechanism is conducted by at least a pair of strain gage members.

* * * * *